United States Patent [19]

Cytron

[11] Patent Number: 5,792,661
[45] Date of Patent: Aug. 11, 1998

[54] METHOD OF DETECTING LEAKS IN SEALED CONTAINERS

[75] Inventor: Sheldon J. Cytron, Mountain Lakes, N.J.

[73] Assignee: The United States of America as represented by the Secretary of the Army, Washington, D.C.

[21] Appl. No.: 828,526

[22] Filed: Mar. 31, 1997

[51] Int. Cl.$^6$ ................................................. G01N 31/22
[52] U.S. Cl. ................................................. 436/3; 436/121
[58] Field of Search ........................... 436/3, 1, 27, 56, 436/121

[56] References Cited

U.S. PATENT DOCUMENTS

| | | | |
|---|---|---|---|
| 1,905,817 | 4/1933 | Dobrovolny et al. | 436/3 |
| 2,094,270 | 9/1937 | Hampton et al. | 436/3 |

OTHER PUBLICATIONS

The Merk Index, tenth edition, pp. 697–698, 1983.

*Primary Examiner*—Lyle A. Alexander
*Attorney, Agent, or Firm*—John F. Morgan; John E. Callaghan

[57] ABSTRACT

An apparatus and method for detecting a leak by mixing an amount of odorant with the contents of a sealed container. An amount of odorant having a detectable odor is mixed with the contents of a sealed container. The sealed container with the odorant is placed within a detection zone which is monitored to detect the presence of the odorant which would indicate leakage of the container's contents. The detection zone defines an area within which leakage of the contents will produce a detectable quantity of the odorant. The odorant may be a gas. Preferred odorants are selected from the group consisting of sulfides, cyclic sulfides and mercaptans. In a sealed light source device having radioactive tritium gas, the preferred odorant is hydrogen sulfide which is detectable by individuals in concentrations of at least 5 parts-per-billion (ppb). Individuals, which may be part of a scheduled roving sentry or a patrol, monitor for the presence of the odorant in the detection zone. Mechanical, optical-mechanical, or other such devices may also be used to monitor the presence of the odorant within the detection zone.

3 Claims, No Drawings

METHOD OF DETECTING LEAKS IN SEALED CONTAINERS

U.S. GOVERNMENT INTEREST

The invention described herein may be manufactured, used and licensed by or for the U.S. Government for U.S. Government purposes.

FIELD OF THE INVENTION

The present invention relates to an apparatus and method of detecting a leak in a sealed container. More specifically, the present invention relates to an apparatus and method of detecting a leak by mixing an amount of odorant with the contents of a sealed container.

BACKGROUND OF THE INVENTION

The United States Department of Defense presently has many thousands of Curies of radioactive tritium gas confined in sealed light source devices distributed throughout the world. Such self-powered radioluminescent (RL) devices have been used to provide small, reliable non-electrical illumination for numerous systems since the 1970's.

These RL devices are constructed of sealed glass vials containing tritium gas under pressure. The inner surfaces of the glass vials are coated with phosphors and portions of the exterior surfaces of the vials are painted to enhance luminosity. As the tritium radioactively decays, it emits beta particles that energize the phosphor coatings to radiate light and provide the required illumination. The phosphors coating the inside of the glass vials must not be contaminated to prevent illumination degradation.

Although these RL devices perform well under normal service, unnecessary rough handling and improper maintenance procedures can result in accidental breakage or cracking of the pressurized glass vials. The subsequent release of radioactive tritium gas into the surrounding environment causes contamination of personal and equipment proximate to the breached vial and exposes personnel to unnecessary radiation. Not only is tritium gas odorless, but the RL devices glass vials are usually encased in support fixtures that obscure viewing the vials so that any leakage of the vials can be extremely difficult to detect, especially just after a leak begins.

Failure to promptly detect such tritium leakage from these RL devices requires extensive and costly decontamination procedures for affected personnel, equipment and buildings. Unsuspecting personnel inadvertently exposed to the tritium are also subjected to a potential radiation health hazard.

Several prior methods have been used to detect RL tritium device leakage. One method consists of visually detecting a loss of luminosity from the RL tritium devices. However, this procedure must be conducted in darkened or very low light conditions and is rarely used. Additionally, detection of decreased luminosity is subjective if not performed with controlled measurements, and further there is not usually a base line or initial luminosity of the specific RL tritium device with which to determine any comparative luminosity decrease. This method is useful for any catastrophic or late stage leakage of tritium gas from the vials as any marked decrease of luminosity of the RL devices is relatively easily discerned by even casual observers.

Another seemingly logical method would be to use a radiation survey meter to detect the presence of the beta particles radiated from the tritium in the environment proximate any breached vial. Although normally effective to detect the presence of many other radioactive materials, the detection range for tritium beta radiation is outside the detection ranges of most survey meters as fielded and in use by the U.S. Department of Defense.

The currently accepted method to detect tritium from a leaking RL device is to obtain swipes of the surrounding potentially contaminated area and equipment and conduct time consuming and sophisticated counting techniques to determine if the RL devices are leaking and releasing radioactive tritium gas. Unless a leak is suspected from a specific vial or small number of possible vials, it is extremely time consuming and impractical to use this method to routinely check all RL tritium devices in use.

Therefore most slow RL tritium device leaks go undetected resulting in contamination of equipment, buildings and personnel. The resulting decontamination procedures, if/when the leak is finally detected, is costly and time consuming not to mention the potentially deleterious health affects for contaminated personnel. Only obvious cracks or breaks of the tritium glass vials that can be easily observed, or those vial breaches that release a substantial release of tritium from the vials resulting in a distinct and noticeable decrease in luminosity, will be quickly detected and handled to minimize contamination and personnel exposure.

Accordingly, it is an object of the present invention to provide an apparatus and method to promptly detect leakage from sealed containers.

Another object of the present invention is to provide an apparatus and method to promptly detect even minimal tritium leakage from RL tritium devices.

A further object of the present invention is to provide an apparatus and method to promptly detect tritium leakage from RL tritium devices to allow prompt decontamination of, and to minimize the deleterious health affects upon, contaminated personnel.

Another object of the present invention is to provide an apparatus and method to promptly detect tritium leakage from RL tritium devices to allow prompt decontamination of affected equipment and buildings.

Yet another object of the present invention is to provide an apparatus and method to detect tritium leakage from RL tritium devices by a simple and fool proof means.

Another object of the present invention is to provide an apparatus and method of detecting tritium leakage from RL tritium devices without substantially affecting the normal luminosity of the RL tritium devices.

Other objects will appear hereinafter.

SUMMARY OF THE INVENTION

It has now been discovered that the above and other objects of the present invention may be accomplished in the following manner. Specifically, the present invention provides an apparatus and method for detecting a leak by mixing an amount of odorant with the contents of a sealed container. An amount of odorant will now always be released with the tritium upon developing a lead in a sealed container. The amount of odorant released will develop a detectable odor within a detection zone that fully surrounds the leaking container. Monitoring this detection zone and detecting the presence of this odorant would be a positive indication of leakage of the contents from the once sealed container.

The detection zone defines an area within which leakage of the sealed container will produce a detectable quantity of the odorant. The odorant may be a gas. Preferred odorants are selected from the group consisting of sulfides, cyclic sulfides and mercaptans. In a sealed light source device having radioactive tritium gas, the preferred odorant is hydrogen sulfide which is detectable by individuals in concentrations of at least 5 parts-per-billion (ppb). Individuals, which may be part of a scheduled roving sentry or a patrol, monitor for the presence of the odorant in the detection zone. Mechanical, optical-mechanical, or other devices may also be used to monitor the presence of the odorant within the detection zone.

DETAILED DESCRIPTION OF THE PREFERRED EMBODIMENT

Self-powered radioluminescent (RL) devices utilized by the U.S. Department of Defense employ sealed glass vials filled with tritium gas under pressure. The interior of the glass vials are coated with phosphors, typically sulfide-based compounds such as zinc and cadmium sulfides, which luminesce to provide the desired light when bombarded by the beta particles resulting from the radioactive decay of the tritium gas. Portions of the exterior of the vials are also painted to enhance luminosity. These vials are usually encased in support fixtures for protection and positioned in desired locations, commonly on fire control devises.

It has been discovered that mixing an odorant having a detectable odor with the tritium gas would serve as a warning agent to signal tritium gas leakage from a sealed vial allowing prompt containment of the leak and decontamination and treatment of affected personnel, equipment, and buildings. However, any such odorant must: (1) be non-reactive with the phosphors coated on the interior of the glass vials to avoid reduction in luminosity of the RL device; (2) have chemical and organoleptic properties to be readily detectable in minute quantities and permit a minimal amount to be mixed with the tritium gas so as to not displace too much of the tritium and thus reduce the luminosity of the RL device; and (3) be non-toxic and not create a health hazard upon any subsequent air borne exposure.

To avoid undesirable reactions with the sulfide-based phosphors, the desired odorants may be selected, for example, from the group consisting of sulfides, cyclic sulfides and mercaptans. The preferred odorant is hydrogen sulfide which is a gas at normal operating temperatures for RL devices and is detectable in concentrations as little as 5 ppb. Thus only a relatively minimal quantity of hydrogen sulfide is necessary to be mixed with the tritium gas in the sealed vials to permit sufficient concentrations to allow detection in the detection zone, or area in which leakage of a sealed vial will produce a detectable quantity of the odorant. Hydrogen sulfide has the distinctive odor of 'rotten eggs' in these very small concentrations.

Further, the use of hydrogen sulfide as the odorant will not generate a health hazard upon release into the environment since any airborne exposure will be below the Occupational Health and Safety Act (OSHA) standards for short term exposure. The 5 ppb concentration necessary for detection of hydrogen sulfide is also below the EPA toxic levels while sufficient to persist in the environment surrounding a leaking vial to alert personnel of a tritium release.

Hydrogen sulfide, or another selected odorant, is introduced into the sealed glass vial RL devices during the standard manufacturing process of the RL devices. Briefly, glass vials are blown by traditional methods and are then given a thermal outgassing to clean off their inner surfaces. A binding agent and phosphor powders are introduced into the vials in a manner that allows the phosphors to coat their inner surfaces. The coated vials are then subjected to a baking process to set the phosphors to the vial's interior surfaces and to enhance adhesion to those surfaces.

The vials are then filled with pressurized tritium and the hydrogen sulfide gasses. The concentration of the hydrogen sulfide in the sealed vial is preferably between 200 and 10 ppm. Each gas may be metered to insure correct concentrations. The vials are then sealed and given another bake-out to verify a proper seal and to ensure they meet acceptable standards of luminosity. Portions of the vials exterior surface may then be coated with reflective paint to enhance luminosity.

The resulting RL vials are then normally encased in support fixtures and mounted on desired equipment, usually fire control devices. The area surrounding the vials within which a detectable quantity of the hydrogen sulfide, or other odorant used, will persist is known as the detection zone. The detection zone is monitored for the presence of the odorant. If the odorant is detected within the detection zone signaling a leak from the sealed RL vial, the offending vial is isolated, replaced, and disposed of. The surrounding equipment and area may then be promptly decontaminated to minimize further contamination and personnel may be checked for any contamination to minimize their exposure to tritium.

For example, the detection zone would be the interior of a bunker within which an RL devise made in accordance with the present invention is placed and used. In an aircraft, the detection zone would be a closed cockpit if the RL devise were utilized only in that space, or it could be the entirety of an aircraft's interior if the RL devise were used in a open space behind the cockpit. If an RL devise were used in a relatively large open space, such as in a warehouse, the detection zone would be an area proximate the location of the RL devise within which the concentration of the selected odorant is detectable.

The monitoring is usually conducted by personnel using the equipment to be illuminated by the RL devise or by roving sentry or patrols within the detection zone. Once the distinctive 'rotten eggs' odor of the hydrogen sulfide is detected by the personnel, the proper decontamination steps and replacement of the offending RL devise is accomplished. It will be noted that other types of known monitoring equipment within the detection zone sensitive to hydrogen sulfide, or the selected odorant, may be used. Such monitoring equipment may then sound an audible or visual alarm locally, or at a remote station, further alerting personnel to the presence of the leaking RL devise vial. Preferably, after the leaking RL devise is replaced, the proximate area is aired out to remove the offending odor and to prevent false alarms. It is noted that in any case it is anticipated that the odorant will eventually naturally dissipate, eliminating the detection zone.

It is appreciated that other odorants, selected from the group described above, may be used instead of hydrogen sulfide with the RL tritium devices in a like manner. Also, the apparatus and method disclosed herein may be used for any sealed container generally and the odorant may consist of liquids, granulated solids, or gasses as long as the selected odorant escapes from the container in a quantity sufficient to create an odor within the detection zone.

While particular embodiments of the present invention have been illustrated and described, it is not intended to limit the invention, except as defined by the following claims.

I claim:

1. In a method for detecting leaks of tritium gas from a self-powered, radioluminescent (RL) device, said device having a sealed glass vial containing tritium gas under pressure and the inner walls of the vial being coated with sulfide-based phosphors which luminesce on reaction with beta radiation produced by radioactive decay of the tritium, the improvement comprising having hydrogen sulfide gas mixed with the tritium in an amount sufficient to act as an odorant in the event of leakage of gases from the vial, the concentration, in the vial being at least 5 and up to 200,000 ppb.

2. The method of claim 1 wherein the phosphors the vial are selected from zinc and cadmium sulfide.

3. The method of claim 2 wherein the concentration of hydrogen, sulfide in the vial is about 10,000 to 200,00 ppb.

* * * * *